(12) United States Patent
Matsuura et al.

(10) Patent No.: US 9,854,809 B2
(45) Date of Patent: Jan. 2, 2018

(54) SEAMLESS CAPSULE FOR EXTERMINATION OF HARMFUL INSECTS

(71) Applicants: MORISHITA JINTAN CO., LTD., Osaka-shi, Osaka (JP); KYOTO UNIVERSITY, Kyoto-shi, Kyoto (JP)

(72) Inventors: Kenji Matsuura, Kyoto (JP); Ryosei Kamaguchi, Hirakata (JP); Daisuke Tagawa, Hirakata (JP); Taku Hashimoto, Hirakata (JP); Masaaki Nakatsuji, Hirakata (JP)

(73) Assignees: MORISHITA JINTAN CO., LTD., Osaka (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/026,906

(22) PCT Filed: Oct. 3, 2014

(86) PCT No.: PCT/JP2014/076606
§ 371 (c)(1),
(2) Date: Apr. 1, 2016

(87) PCT Pub. No.: WO2015/050255
PCT Pub. Date: Apr. 9, 2015

(65) Prior Publication Data
US 2016/0278387 A1  Sep. 29, 2016

(30) Foreign Application Priority Data
Oct. 4, 2013  (JP) .................................. 2013-209440

(51) Int. Cl.
| A01N 63/02 | (2006.01) |
| A01M 1/02 | (2006.01) |
| A01M 1/20 | (2006.01) |
| A01N 25/28 | (2006.01) |
| A01N 43/54 | (2006.01) |
| A01N 57/20 | (2006.01) |

(52) U.S. Cl.
CPC .............. *A01N 63/02* (2013.01); *A01M 1/02* (2013.01); *A01M 1/20* (2013.01); *A01N 25/28* (2013.01); *A01N 43/54* (2013.01); *A01N 57/20* (2013.01); *A01M 2200/011* (2013.01)

(58) Field of Classification Search
CPC ........ A01N 25/28; A01N 57/20; A01N 43/54; A01N 63/02; A01M 1/02; A01M 1/20; A01M 2200/011
USPC ...................................................... 424/408
See application file for complete search history.

(56) References Cited

U.S. PATENT DOCUMENTS

2010/0028323 A1  2/2010 Matsuura et al.
2010/0093882 A1  4/2010 Ohama
2012/0282214 A1  11/2012 Matsuura et al.
2014/0259881 A1  9/2014 Matsuura et al.
2014/0328886 A1  11/2014 Matsuura et al.

FOREIGN PATENT DOCUMENTS

| EP | 2111755 | 10/2009 | |
| EP | 2289315 | 3/2011 | |
| JP | 2000-342149 A | 12/2000 | |
| JP | 2008-194007 A | 8/2008 | |
| JP | WO 2011059054 A1 * | 5/2011 | .............. A01M 1/02 |
| JP | 2012-97262 A | 5/2012 | |
| WO | 2011/059054 A1 | 5/2011 | |
| WO | WO2011059045 A1 * | 5/2011 | |
| WO | 2013/073676 A1 | 5/2013 | |

OTHER PUBLICATIONS

International Preliminary Report on Patentability and Written Opinion, and English translation, PCT/JP2014/076606, dated Apr. 5, 2016 (6 pages).
International Search Report issued in PCT/JP2014/076606 dated Jan. 13, 2015.
Matsuura et al., "Cuckoo fungus mimics termite eggs by producing the cellulose-digesting enzyme β-glucosidase", Current Biology, vol. 19, No. 1, pp. 30-36, 7 pages.
Matsuura et al., "Symbiosis of a termite and a sclerotium-forming fungus: Sclerotia mimic termite eggs", Ecological Research, vol. 15, No. 4, pp. 405-414, 10 pages.
Matsuura, "Termite-egg mimicry by a sclerotium-forming fungus", Proceedings of the Royal Society B, vol. 273, No. 1591, pp. 1203-1209, 7 pages.
The Extended European Search Reported of European patent application No. 14850196.8, dated May 4, 2017, 11 pages provided.

* cited by examiner

*Primary Examiner* — Johann R Richter
*Assistant Examiner* — Courtney Brown
(74) *Attorney, Agent, or Firm* — Hamre, Schumann, Mueller & Larson P.C.

(57) ABSTRACT

The present invention provides a seamless capsule for exterminating insect pests, particularly the capsule effective for termites, which hardly affects an ecological system other than the insect pests, such as a human being and domestic animals and useful insects around the human being, has an excellent safety and an excellent transporting rate by insect pests, particularly termites and has an improved exterminating efficiency per number of capsules transported or per unit time, and a method of exterminating insect pests by using the seamless capsule. The present invention relates to a seamless capsule for exterminating insect pests, wherein the seamless capsule imitates an egg of an insect pest and the seamless capsule comprises a content material to be enclosed and a shell film material layer including the content material therein, wherein an active ingredient for exterminating insect pests is contained in the content material and/or the shell film material layer, an egg recognition pheromone is coated on the surface of the seamless capsule, and the seamless capsule has a surface roughness (Ra) of 0.005 to 5 μm.

8 Claims, 3 Drawing Sheets

SEAMLESS CAPSULE FOR EXTERMINATION OF HARMFUL INSECTS

TECHNICAL FIELD

The present invention relates to a seamless capsule for exterminating insect pests, particularly termites and a method of exterminating insect pests by using the seamless capsule.

BACKGROUND OF THE INVENTION

With respect to extermination of insect pests, various methods of exterminating insect pests have been developed. In particularly, since termites seriously damage wooden houses, an agent for and a method of exterminating the termites have been researched and developed throughout the world. As the method of exterminating the termites, a method of exterminating the termites by injecting a solution-type drug, such as an organophosphate, a carbamate, a pyrethroid, into sites which the termites intrude, or a method of exterminating the termites by fumigation of methyl bromide and the like (for example, see Non-Patent Document 1).

As an alternative to the treatment method based on spraying pesticides, a bait method is known in which slow-acting, insecticidal active ingredients are mixed into a bait, and the bait is allowed to be eaten by termites, thereby exterminating them (See, for example, Non-Patent Document 2).

Techniques which have been heretofore used for exterminating insect pests, especially termites, are those that basically, a large amount of insecticide is put in from the outside of insect pest-damaged wood so as to exterminate the insect pests, and thus lead to health damages to human body and environmental pollution. In addition, there is a problem that damages are spread in other places when even a portion of the termites' colony remains surviving. It is the most serious problem that labor costs required for extermination with these techniques are too high. The method for exterminating insect pests which is frequently carried out is a fumigation process using methyl bromide, but it is a substance causing the destruction of the ozone layer and thus, in these days, results in enhanced movements to regulate its use.

As methods for exterminating ants which organize a social life as with the termites, a method is effective, in which a bait that an ants' favorite food is mixed into poisonous materials is given to ants and allowed to be taken back into their nest, thereby killing the whole population within the nest. However, the bait method in which poisonous baits are employed for allowing termites to transport insecticides from the outside to the inside of their nest are not always effective, because termites eat wood itself where they build a nest. In particular, it is difficult to completely exterminate termites of the genus *Reticulitermes* by the bait method (see, for example, Non-Patent Document 2).

As a method of more efficiently allowing insect pests to ingest an active ingredient than the bait method, "a method of exterminating insect pests by transportation of an imitation egg" using an instinct to transport eggs that is basic social behavior of insect pests have been developed (Patent Document 1). The insect pests in this method were termites. In this method, it was possible to allow termites to transport imitation eggs using crude extractives from eggs of termites, but an egg recognition pheromone of termites was not identified. There is a big problem in terms of cost to carry out such a method unless a large amount of the egg recognition pheromone can be inexpensively produced by identifying the egg recognition pheromone.

The present inventors identified that a main component of the egg recognition pheromone was a lysozyme, a lysozyme salt, a biological fragment of a lysozyme or a lysozyme-related peptide, and proposed an imitation egg formed by a combination of the egg recognition pheromone and an agent for exterminating termites (Patent Document 2). The imitation egg was transported in a nest by the termites, and it was recognized that effects of exterminating the termites were accomplished. However, since the agent for exterminating termites is present on the surface of the imitation egg, a transporting rate of the imitation egg by the termites is not sufficient. In addition, since there was a possibility adversely affecting a human being, which uses the agent for exterminating the insect pests and a method of exterminating insect pests by using the agent, and domestic animals and useful insects around the human being, safety was not sufficient, and there was a room to further enhance a performance as an agent for exterminating insect pests.

The present inventors studied a type of a substrate of the imitation egg, and confirmed the fact that a transporting rate of the imitation egg by the termites is very high in case of inorganic materials, particularly a glass as the substrate and a transporting rate which is as high as the rate in case of the glass was not obtained in case of other materials. However, it is difficult to contain an active ingredient for exterminating insect pests in the imitation egg, of which the substrate is an inorganic material. Therefore, in case of using only glass beads, since it is necessary to directly apply the active ingredient for exterminating insect pests as an agent on the surface of the glass beads, there is a limit to the agent amount that can be applied. In addition, since termites evade the agent, the termites do not transport the glass beads. An egg recognition pheromone of termites is also applied on the surface of the glass beads, but it is difficult to fix the egg recognition pheromone thereon. Therefore, when humidity is high in an installation location of the imitation eggs, since the egg recognition pheromone is easily carried away with water due to dew condensation on the surface of the glass beads, the termites do not recognize the glass beads as eggs of the termites, and the termites do not transport the glass beads. In order to solve the problems, the present inventors proposed an agent for exterminating insect pests, of which an active ingredient for exterminating insect pests is formed into a capsule of a material such as gelatin that the active ingredient is easily contained and is mixed with the imitation eggs (Patent Document 3). However, in the above technology, since the imitation eggs containing no active ingredient for exterminating insect pests are mixed with the capsules containing the active ingredient, there is a room to improve an efficiency of exterminating insect pests.

PRIOR ART

Patent Documents

Patent Document 1: JP 2000-342149 A
Patent Document 2: JP 2008-194007 A
Patent Document 3: P2011-250994 (Japanese Patent Application No. 2011-250994)

Non-patent Documents

Non-Patent Document 1: "Termites and Control Measures", Corporation Aggregate Japan Termite Control Association, 2000, p. 219

Non-Patent Document 2: "Activity Evaluation of Japanese Subterranean Termites Using Monitoring Stations and Control by Bait Methods", Recent Developments of Monitoring Technologies of Insect Ecology in Sustainable Humanmosphere, 2006, p. 48.

OBJECTS OF THE INVENTION

The present inventors have intensely studied an agent for exterminating insect pests composed of only capsules of a material that an active ingredient for exterminating insect pests is easily contained and have found that there are capsules transported by termites even if they are the above capsules alone; and a transporting rate of the capsules by insect pests, particularly termites varies depending on properties of the capsule. Based on the above finding, a main object of the present invention is to obtain an agent for exterminating insect pests, particularly an exterminating agent effective for termites, which hardly affects an ecological system other than the insect pests, such as a human being, domestic animals and useful insects around the human being, has an excellent transporting rate by insect pests, particularly termites and has an improved efficiency of exterminating insect pests per number of capsules transported or per unit time.

SUMMARY OF THE INVENTION

The present invention relates to a seamless capsule for exterminating insect pests, wherein the seamless capsule imitates an egg of an insect pest and the seamless capsule comprises a content material to be enclosed and a shell film material layer including the content material therein, wherein an active ingredient for exterminating insect pests is contained in the content material and/or the shell film material layer, an egg recognition pheromone is coated on the surface of the seamless capsule, and the seamless capsule has a surface roughness (Ra) of 0.005 to 5 µm.

In order to suitably carry out the present invention, it is desired that:

the seamless capsule for exterminating insect pests has a Young's modulus of 0.392 MPa to $20.6 \times 10^4$ MPa;

the seamless capsule for exterminating insect pests has a density of 0.5 to 9.0 $g/cm^3$;

the seamless capsule for exterminating insect pests has a diameter of 250 to 600 µm;

the seamless capsule for exterminating insect pests comprises a protective layer formed from a shell film inner layer material between the content material and the shell film material layer; and the insect pests are termites.

As another embodiment, the present invention relates to a method of exterminating insect pests, wherein a seamless capsule imitating an egg of an insect pest for exterminating insect pests comprising a content material to be enclosed and a shell film material layer including the content material therein, wherein an active ingredient for exterminating insect pests is contained in the content material and/or the shell film material layer, an egg recognition pheromone is coated on the surface of the seamless capsule, and the seamless capsule has a surface roughness (Ra) of 0.005 to 5 µm is supplied to the insect pests, and is transported in a nest by utilizing an egg transporting behavior of the insect pests.

EFFECTS OF THE INVENTION

According to the present invention, it is possible to provide a seamless capsule imitating an egg of an insect pest for exterminating insect pests, particularly the seamless capsule effective for termites in which an egg recognition pheromone is coated on the surface thereof, which has an improved exterminating efficiency per number of capsules transported or per unit time, and (1) (i) hardly affects an ecological system other than the insect pests, such as a human being, which uses the seamless capsule for exterminating insect pests, and domestic animals and useful insects around the human being, and has an excellent safety, (ii) has an excellent transporting rate by insect pests, particularly termites, because the insect pests do not contact with the active ingredient for exterminating them when transporting the capsule, by composing of only capsules of a material, in which an active ingredient for exterminating insect pests is easily contained, that is, by containing the active ingredient for exterminating insect pests in the seamless capsule; and (2) has an excellent transporting rate by insect pests, particularly termites by adjusting a surface roughness (Ra) to a specified range.

DESCRIPTION OF THE PREFERRED EMBODIMENTS

Figure 1:
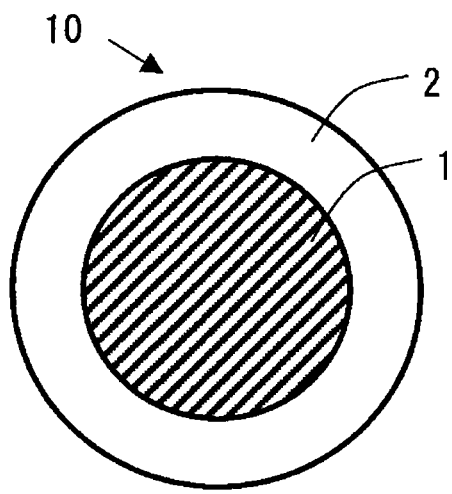
FIG. 1 is a schematic section illustrating one embodiment (two-layered structure) of the seamless capsule for exterminating insect pests of the present invention.

The seamless capsule for exterminating insect pests of the present invention is a particulate agent for exterminating insect pests imitating an egg of an insect pest comprising a content material to be enclosed and a shell film material layer including the content material therein, wherein an active ingredient for exterminating insect pests is contained in the content material and/or the shell film material layer, an egg recognition pheromone is coated on the surface thereof, and the seamless capsule has a surface roughness (Ra) of 0.005 to 5 µm. The seamless capsule for exterminating insect pests of the present invention and a method of exterminating the insect pests by using the seamless capsule will be explained as follows.

An insect having a nature of transporting eggs, such as termite has a nature that the insect transports eggs in a nest and arranges the eggs into piles, takes care of the eggs by licking the surface of eggs and the like, or performs trophallaxis between individuals. It is possible to exterminate insect pests by utilizing the nature. For example, termites recognize imitation eggs having a size and shape similar to the true eggs and coated on the surface thereof with an egg recognition pheromone as the true eggs, and transport the imitation eggs into their own egg mass in the nest. The termites perform an action of taking care of the eggs, for example, licking the eggs and the like and perform trophallaxis between individuals in the nest. Therefore, it is possible to efficiently destroy a genitospinal center of a colony by allowing the termites to transport particles containing an active ingredient such as an insecticidal active ingredient, a hatch inhibitor, a reproductive inhibitor, an ingredient with growth inhibiting activity and the like into the egg mass together with the imitation eggs.

The insect pests, which can be exterminated by the seamless capsule of the present invention and the method of exterminating insect pests with the seamless capsule, may be any insect pests as long as they have an instinct to transport eggs. The insect pests, to which the seamless capsule and the method of exterminating insect pests with the seamless capsule of the present invention are suitably applicable, are termites. The termites exterminated by the seamless capsule and the method of the present invention may be any type of termite, and termites not only in Japan but also around the world can become an object thereof. Examples of the typical termites exterminated by the seamless capsule and the method of the present invention include *Reticulitermes speratus, Coptotermes formosanus* and the like, but are not limited thereto. The "extermination of insect pests" as used herein includes "prevention of insect pests". The "insect pest" as used herein means an insect, which harmfully affect human beings, domestic animals, agricultural crops, possessions and the like.

In the seamless capsule imitating an egg of an insect pest for exterminating insect pests coated on the surface thereof with an egg recognition pheromone of the present invention, a main component of the egg recognition pheromone used is, for example, a lysozyme, a lysozyme salt, a biological fragment of a lysozyme or a lysozyme-related peptide. The lysozyme may be derived from any biological species, for example, mammals, birds such as a chicken, fishes, reptiles, amphibians, insects such as a silkworm and the like. Examples of preferable lysozymes, which are inexpensively obtained in a large amount and can be used in the present invention, include a lysozyme derived from chicken egg-white. A lysozyme derived from an extract from a termite egg may be used in the present invention. The lysozyme used in the present invention may be purified or not. In addition, the lysozyme used in the present invention may be produced by a gene recombination process. It is well known for a person with ordinary skill in the art to produce a protein, polypeptide or peptide by the gene recombination process. A desired protein can be obtained by linking a gene of a desired protein to a vector, and transferring it into appropriate host cells, such as a colibacillus, a yeast and then growing it. Type of the vector and host cells, a condition of transferring the vector, a condition of cultivating the host cells, methods of separating and purifying the desired protein and the like can be suitably selected from materials or methods well known by a person with ordinary skill in the art.

The lysozyme may be in the form of a salt. The lysozyme salt may be a salt with any substance that can form a salt, for example, a salt with an organic acid, a salt with an inorganic acid, a salt with an organic base, or a salt with an inorganic base. In addition, for example, β- or γ-carboxyl group of asparagine acid or glutamine acid constituting the lysozyme and a metal such as sodium or potassium may form the salt. Further, for example, a salt may be formed in a side chain of a basic amino acid constituting the lysozyme. A biological fragment of lysozyme or a lysozyme-related peptide may be in the form of a salt.

Moreover, the biological fragment of lysozyme may be used as an egg recognition pheromone. The biological fragment of lysozyme refers to a polypeptide or a peptide having a partial amino acid sequence of lysozyme, which has an egg recognition activity similar to lysozyme. Since such fragment is a short chain, it is suitable for large-scale production by a gene recombination method.

Furthermore, the lysozyme-related peptide may be used as an egg recognition pheromone. The Lysozyme-related peptide refers to a protein, a polypeptide or a peptide having an egg recognition activity similar to lysozyme, which is different from lysozyme and the biological fragment of lysozyme. The lysozyme-related peptide may be derived from a natural source or may be a synthetic compound. The lysozyme-related peptide may have an amino acid sequence different from the natural lysozyme by a technique such as a site-directed mutagenesis method. For example, lysozyme, a biological fragment of lysozyme or a lysozyme-related peptide having an amino acid sequence such that termites further like may be formed to be used in the present invention. Further, for example, lysozyme, a biological fragment of lysozyme or a lysozyme-related peptide having an amino acid sequence that has high specificity to a particular type of termite may be formed to be used in the present invention.

Examples of a main component of another egg recognition pheromone used in the seamless capsule for exterminating insect pests of the present invention include, for example, β-glucosidase, a biological fragment of β-glucosidase or a β-glucosidase-related peptide. The β-glucosidase is widely distributed in microorganisms, plants and animals, and may be derived from any specie. Examples thereof include, but are not limit to, for example, plants such as almonds, cycads and the like; animals such as termites, edible cockroaches, snails and the like; microorganisms, such as *Aspergillus oryzae*, yeasts, enterococci, Bacilli and the like; as its origin. The β-glucosidase may not be purified or may be purified. Furthermore the β-glucosidase may be one which is produced by a gene recombination method. It is well known for a person with ordinary skill in the art to produce a protein, a polypeptide or a peptide by a gene recombination method. In general, a desired protein can be obtained by linking a gene of a desired protein to a vector, and transferring it into appropriate host cells, such as a colon bacillus, a yeast fungus and then growing it. Type of the vector and host cells, a condition of transferring the vector, a condition of cultivating the host cells, methods of separating and purifying the desired protein and the like can be suitably selected from materials or methods well known by a person with ordinary skill in the art.

As a main component of the egg recognition pheromone used in the present invention, β-glucosidase may be in the form of a salt. A salt of β-glucosidase may be a salt with any substance that can form a salt, for example, a salt with an organic acid, a salt with an inorganic acid, a salt with an organic base, or a salt with an inorganic base. For example, β- or γ-carboxyl group of asparagine acid or glutamine acid constituting the β-glucosidase and a metal such as sodium or potassium may form the salt. Further, for example, a salt may be formed in a side chain of a basic amino acid constituting the β-glucosidase. A biological fragment of β-glucosidase or a β-glucosidase-related peptide may be in the form of a salt.

Moreover, in the present invention, the biological fragment of β-glucosidase may be used as an egg recognition pheromone. The biological fragment of β-glucosidase refers to a polypeptide or a peptide having a partial amino acid sequence of β-glucosidase, which has an egg recognition activity similar to β-glucosidase. Since such fragment is a short chain, it is suitable for large-scale production by a gene recombination method.

Furthermore, the β-glucosidase-related peptide may be used as an egg recognition pheromone. The β-glucosidase-related peptide refers to a protein, a polypeptide or a peptide having an egg recognition activity similar to β-glucosidase, which is different from β-glucosidase and the biological fragment of β-glucosidase. The β-glucosidase-related peptide may be derived from a natural source or may be a synthetic compound. The β-glucosidase-related peptide may have an amino acid sequence different from the natural β-glucosidase by a technique such as a site-directed mutagenesis method. For example, β-glucosidase, a biological fragment of β-glucosidase or a β-glucosidase-related peptide having an amino acid sequence such that termites further like may be formed to be used in the present invention. Further, for example, β-glucosidase, a biological fragment of β-glucosidase or a β-glucosidase-related peptide having an amino acid sequence that has high specificity to a particular type of termite may be formed to be used in the present invention.

The seamless capsule imitating an egg of an insect pest for exterminating insect pests of the present invention, which an egg recognition pheromone is coated on the surface thereof, must have a shape, size and nature similar to those of the eggs of the insect pests to be exterminated. The shape and size of the seamless capsule for exterminating insect pests used in the present invention are selected so as to imitate those of the actual eggs of the insect pests.

It is desired that the seamless capsule for exterminating insect pests of the present invention comprising the content material to be enclosed as an active ingredient for exterminating insect pests has a diameter of 250 to 600 μm, preferably 400 to 600 μm, more preferably 450 to 550 μm when the capsule has a spherical shape.

When the insect pests are termites, the seamless capsule for exterminating insect pests can have an elongated egg-shape or a spherical shape. When it has the elongated egg-shape, it is desired that a short diameter of the seamless capsule is equal to or slightly larger than a short diameter of an egg of the termite to be exterminated. When exterminating termites, of which an egg has a short diameter of, for example, about 250 to about 450 μm, the seamless capsule for exterminating insect pests of an elongated egg-shape may have a short diameter of about 250 to about 600 μm, preferably about 400 to about 550 μm, more preferably about 450 μm. In addition, when it has the spherical shape, it is desired that a diameter of the seamless capsule is equal to or slightly larger than a short diameter of an egg of the termite to be exterminated. When exterminating termites, of which an egg has a short diameter of, for example, about 250 to about 450 μm, the seamless capsule for exterminating insect pests of a spherical shape may have a diameter of about 250 to about 600 μm, preferably about 400 to about 600 μm, more preferably about 450 to about 550 μm. It is desired that the seamless capsule for exterminating insect pests has a spherical shape because it is easily formed.

It is desired that the seamless capsule for exterminating insect pests comprising the content material to be enclosed as an active ingredient for exterminating insect pests of the present invention has a surface roughness (Ra) of 0.005 to 5 μm, preferably 0.01 to 3 μm, more preferably 0.02 to 2 μm. When the surface roughness (Ra) is lower than 0.005 μm, the seamless capsule is slippery even if the termite holds the seamless capsule, and the termite does not carry the seamless capsule. On the other hand, when the surface roughness (Ra) is higher than 5 μm, the termite does not recognize the seamless capsule as an egg of the termite, and does not carry the capsule. The surface roughness (Ra) is calculated from a data measured by an image analysis with a shape analysis laser microscope ("VK-X100" or "VK-X200" manufactured by Keyence Corporation) using as a measurement sample the seamless capsule for exterminating insect pests comprising the content material to be enclosed as an active ingredient for exterminating insect pests.

It is desired that the seamless capsule for exterminating insect pests comprising the content material to be enclosed as an active ingredient for exterminating insect pests of the present invention has a Young's modulus of 0.392 MPa to $20.6 \times 10^4$ MPa (40 gf/mm$^2$ to $21.0 \times 10^6$ gf/mm$^2$), preferably 0.441 to 10.0 MPa, more preferably 0.470 to 8.0 MPa. When the Young's modulus is lower than 0.392 MPa, the termite does not recognize the seamless capsule as an egg of the termite, and does not carry the capsule. On the other hand, when the Young's modulus is higher than $20.6 \times 10^4$ MPa, the termite does not recognize the seamless capsule as an egg of the termite, and does not carry the capsule. The Young's modulus is calculated from a measured value of a slope in a stress-strain diagram obtained by a compression test as a mechanical testing process with a particle hardness tester ("GRANO" manufactured by Okada Seiko Co., Ltd.) using as a measurement sample the seamless capsule for exterminating insect pests comprising the content material to be enclosed as an active ingredient for exterminating insect pests.

It is desired that the seamless capsule for exterminating insect pests comprising the content material to be enclosed as an active ingredient for exterminating insect pests of the present invention has a density of 0.5 to 9.0 g/cm$^3$, preferably 0.8 to 7.0 g/cm$^3$, more preferably 1.0 to 4.0 g/cm$^3$. When the density is lower than 0.5 g/cm$^3$, since a weight per unit volume is insufficient, the termite does not recognize the seamless capsule as an egg of the termite, and does not carry the capsule. On the other hand, when the density is higher than 9.0 g/cm$^3$, a weight per unit volume is too high, and the termite cannot carry the capsule. The density is determined by directly measuring a volume and a mass of the seamless capsule for exterminating insect pests comprising the content material to be enclosed, which is an active ingredient for exterminating insect pests, as a sample solid by a method of measuring the density based on geometric measurements according to JIS 8807 and calculating a density from the volume and mass.

In the seamless capsule for exterminating insect pests of the present invention, chemical properties, particularly egg recognition pheromone also need to be identical with or similar to those of natural eggs of insect pests, in addition to the shape and size as described above, and further the physical properties such as a weight and hardness. That is, when coating the egg recognition pheromone on the surface of the shell film material layer of the seamless capsule for exterminating insect pests, it is necessary that these materials appear on the surface.

In the present invention, a seamless capsule imitating an egg of an insect pest for exterminating insect pests is formed by coating the egg recognition pheromone on the surface thereof, and the seamless capsule for exterminating insect pests comprises a content material to be enclosed and at least one shell film material layer including the content material therein. As a method of coating the egg recognition pheromone on the shell film material layer, various methods are well known to a person with ordinary skill in the art, and the shell film material layer may be dredged with, dipped in, applied with, or sprayed with the egg recognition pheromone. In that case, it is preferable from the viewpoint of easy coating and uniform coating to use solutions of the egg recognition pheromone dissolved in a hydrophilic solvent such as a aqueous solution, glycerol, polyethylene glycol, propylene glycol and the like, or dispersions thereof dispersed in a lipophilic solvent such as N, N-dimethylformamide. Furthermore, since methods of immobilizing proteins, polypeptides or peptides to the solid support are well known, such methods may be applied thereto. Examples of the immobilization methods include, for example, an adsorption method, a covalent binding method, an ionic binding method, and an inclusion method.

An amount of the egg recognition pheromone coated on the shell film material layer of the seamless capsule imitating an egg of an insect pest for exterminating insect pests of the present invention can be easily determined by a person with ordinary skill in the art depending on factors, such as types thereof (an organism derived), physicochemical properties thereof, types of the insect pest, types and amounts of the active ingredient for exterminating insect pests, types and degrees of desired effects and the like.

It is also preferable to incorporate glycerol and/or cellulase into the shell film material layer in order to maintain an activity as the egg recognition pheromone in the seamless capsule for exterminating insect pests of the present invention and keep the egg recognition pheromone on the surface of the shell film material layer. The glycerol and cellulase are not always necessary to use a high-purity product. Contents of the glycerol and cellulase in the shell film material layer can be determined depending on factors, such as types, natures and amounts of lysozyme to be used, types of the insect pest, types and amounts of the active ingredient for exterminating insect pests, types and degrees of desired effects and the like.

Furthermore, it is also preferable to contain a component extracted from eggs of target insect pests in the shell film material layer of the seamless capsule for exterminating insect pests of the present invention. Thereby, it is possible to obtain a higher egg transportation effect. Crude extracts from the eggs may be contained in the shell film material layer, or a purified product of the extracts may be contained in the shell film material layer. The content of the crude extract or purified product thereof in the shell film material layer can be determined depending on factors, such as types, natures and amounts of the egg recognition pheromone to be used, types of the insect pest, types and degrees of desired effects and the like. As a method of extracting active ingredients from eggs of insect pests and a method of purifying the extracted active ingredients, methods that are well known in the art can be used.

An active ingredient for exterminating insect pests which can be used in the seamless capsule for exterminating insect pests of the present invention and the method of exterminating insect pests by using the seamless capsule may be any ingredient as long as it can be accomplished to exterminate insect pests. For example, the active ingredient for exterminating insect pests may be an ingredient which perturbs the behavior of insect pests to finally destroy the colony. Examples of the active ingredient for exterminating insect pests suitable for exterminating insect pests include an insecticidal active ingredient, a hatching inhibitor, a procreation inhibitor or a growth inhibitor. Types and amounts of the active ingredient for exterminating insect pests that can be used in a particulate agent for exterminating insect pests containing the active ingredient for exterminating insect pests of the present invention can be selected depending on factors, such as types of the active ingredient for exterminating insect pests, types of the insect pest, types and degrees of desired activity (a damage to be given to the insect pests) and the like. Types and amounts of the active ingredient for exterminating insect pests typically are selected such that it can fully exhibit the desired effect to the desired insect pests. In the seamless capsule for exterminating insect pests of the present invention, since the active ingredient for exterminating insect pests is encapsulated in the seamless capsule as described above, the transporting rate by insect pests of the seamless capsule for exterminating insect pests is not reduced, and it does not adversely affect a human being using the seamless capsule for exterminating insect pests of the present invention and method of exterminating insect pests by using the seamless capsule, and domestic animals and useful insects around the human being.

The active ingredients for exterminating insect pests used in the seamless capsule for exterminating insect pests of the present invention may be used alone or in combination of two or more thereof. For example, insecticidal active ingredients, such as pyrethroid compounds, organophosphorus compounds, carbamate compounds, N-aryl-diazole compound, a hydrazone compound, a sulfonamide compound, natural insecticidal ingredients and the like can be used. In addition, insect growth controlling agents, such as chitin synthesis inhibitors, juvenile hormone-like active compounds, molting hormone-like active compounds and the like can be used as an active ingredient for exterminating insect pests. The active ingredient for exterminating insect pests which can be used in the present invention is of course not limited to the above compounds.

In the seamless capsule for exterminating insect pests of the present invention, it is preferable that the active ingredient for exterminating insect pests is slow-acting. As mentioned above, insect pests such as termites recognize the seamless capsules for exterminating insect pests which have the size and shape similar to the original egg and contain egg recognition pheromone on the surface as eggs, and transport the seamless capsules for exterminating insect pests into their own egg mass. At that time, insect pests take in the active ingredient for exterminating insect pests from the seamless capsule for exterminating insect pests through an action of taking care of the seamless capsule, such as licking the surface thereof.

When some individuals of the insect pest in its colony take in the active ingredient for exterminating insect pests, the active ingredient would spread over a whole of the colony through frequent trophallaxis from stomodeal food by mouth-to-mouth feeding and proctodeal food. Therefore, it is preferable that the active ingredient for exterminating insect pests used in the present invention does not show the effects thereof when transporting the seamless capsule for exterminating insect pests or immediately after the insect pest take in the active ingredient; or shows only the effects thereof to such a degree that the transporting behavior of the seamless capsules and trophallaxis behavior are not adversely affected; and shows the effects thereof after the seamless capsule for exterminating insect pests are transported to the nest and the trophallaxis is conducted between the individuals. By using such a slow-acting active ingredient for exterminating insect pests, it is possible to efficiently exterminate many individuals in the target colony, and an amount of the active ingredient for exterminating insect pests used can be reduced. Therefore, it also has little adverse effect on another ecological system. Examples of the slow-acting active ingredient for exterminating insect pests which can be used in the seamless capsule for exterminating insect pests of the present invention, which are not limited thereto, include, for example, a slow-acting insecticidal ingredient, such as hydramethylnon and the like; a slow-acting hatching inhibitor; a slow-acting procreation inhibitor; a slow-acting growth inhibitor; and the like.

In the seamless capsule for exterminating insect pests of the present invention, it is preferable that the shell film material layer is formed from a controlled-release material. The seamless capsule for exterminating insect pests, of which the active ingredient for exterminating insect pests is gradually released after transporting into the nest, and is incorporated into the insect pests by forming the above shell film material layer from a controlled-release material.

Figure 2:
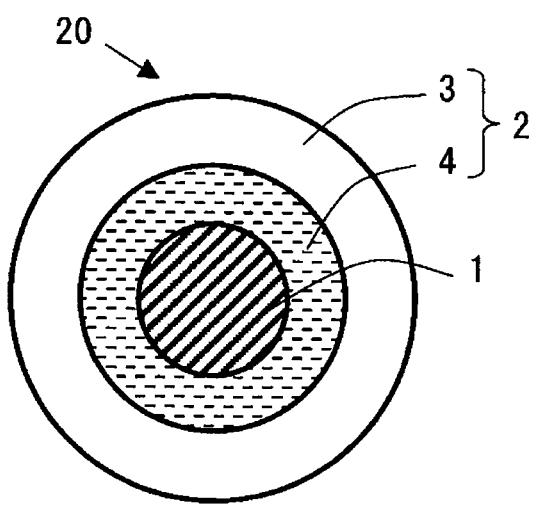
FIG. 2 is a schematic section illustrating another embodiment (three-layered structure) of the seamless capsule for exterminating insect pests of the present invention.

Hereinafter, the seamless capsule for exterminating insect pests comprising the active ingredient for exterminating insect pests of the present invention will be described further in detail with reference to FIG. 1 to FIG. 2. FIG. 1 is a schematic section illustrating one embodiment (two-layered structure) of the seamless capsule for exterminating insect pests of the present invention. FIG. 2 is a schematic section illustrating another embodiment (three-layered structure) of the seamless capsule for exterminating insect pests of the present invention. The seamless capsule comprises a content material to be enclosed 1 as an active ingredient for exterminating insect pests and at least one shell film material layer 2 including the content material therein. The simplest structure as a form of the seamless capsule is a two layer-structured seamless capsule having one shell film material layer 2 as shown in FIG. 1.

In case of forming a shell film material layer 2 as described above, examples of a substrate of the layer include natural polymers such as gelatin, agar, carrageenan, cellulose, chitin, chitosan, starch hydrolysate, shellac, alginic acid; a single component of the synthetic polymers such as acrylate-based oligomers, methacrylate-based oligomers, unsaturated polyester-based oligomers, unsaturated polyester-based oligomers, vinylether-based oligomers, unsaturated polyamide-based oligomers; or the combinations of two or more thereof. From the point of view of repellency and transportability of termites, controlled-release and an environmental influence of the active ingredient for exterminating insect pests and the like, gelatin, cellulose, chitin, chitosan and a methacrylate-based oligomer are preferable, and gelatin and chitosan are more preferable.

As the substrate of the shell film material layer 2, a substrate gellable due to a temperature change or an ultraviolet irradiation at the time of preparing seamless capsules is desired. The substrate gellable due to the temperature change may be a thermoplastic substrate or a thermosetting substrate.

In case of using gelatin as a substrate of the shell film material layer 2, it is preferable to cross-link the substrate by treating with an aldehyde as a cross-linking agent after preparing the seamless capsule, and inactivating the aldehyde with a neutralizing agent to dry it after the cross-linking reaction from the point of view of the strength, Young's modulus and transportability of the seamless capsule. The aldehyde used as the cross-linking agent is preferably glutaraldehyde. The neutralizing agent for the aldehyde is preferably a hypochlorous acid, amino acids and/or alkali metal salts thereof. The amino acids and/or alkali metal salts thereof are preferably are soluble in water at least at room temperature, and are more preferably at least one selected from the group consisting of glycine, alanine, arginine, proline and sodium glutamate.

In the shell film material of the seamless capsule, a plasticizer and pigment may be added to the substrate of the shell film. As the plasticizer, it is possible to use a water-soluble polyhydric alcohol or water-soluble derivatives thereof. An amount of the plasticizer is within the range of 1 to 50% by mass, preferably 10 to 30% by mass, based on the total mass of the shell film material layer. When the amount of the plasticizer is smaller than 1% by mass, the plasticity of the shell film cannot be sufficiently obtained. On the other hand, when the amount is larger than 50% by mass, the shell film is easily softened, and the capsules easily adhere to each other.

Examples of the water-soluble polyhydric alcohols and water-soluble derivatives thereof, which are not limited thereto, include glycerin, polyglycerin, sorbitol, ethylene glycol, polyethylene glycol, propylene glycol, polypropylene glycol, ethylene oxide-propylene oxide copolymer, oligosaccharides, sugar ester, glycerides, sorbitan esters and the like.

It is desired that the solid content concentration of the substrate of the shell film is within the range of 1 to 50% by mass, preferably 10 to 30% by mass. When the solid content concentration is lower than 1% by mass, a gelling power of the shell film is low, and a capsule strength is low. On the other hand, when the solid content concentration is higher than 50% by mass, a viscosity of the shell film solution is high, and it is difficult to form the capsule.

Examples of compositions containing the content material to be enclosed of the seamless capsule for exterminating insect pests of the present invention include:

a lipophilic or hydrophilic liquid material, in which the active ingredient for exterminating insect pests is dissolved in a solvent, a suspension or a dispersion of a dispersion medium and a main component powder insoluble in the dispersion medium, or the mixture thereof. It varies depending on a place for using the seamless capsule for exterminating insect pests, but from the point of view of the controlled-release, the suspension or dispersion of the dispersion medium and the main component powder insoluble in the dispersion medium is preferable as the composition containing the content material to be enclosed.

A seamless capsule having a two-layered structure, in which the composition containing the content material to be enclosed is enclosed with the shell film material layer, is formed as a desired capsule by ejecting the composition containing the content material to be enclosed through an inner nozzle of a multiple nozzle and ejecting the shell film material composition through an outer nozzle into a carrier fluid, simultaneously. In order to exhibit a desired controlled-release of the active ingredient for exterminating insect pests in the seamless capsule for exterminating insect pests containing an active ingredient for exterminating insect pests of the present invention, the seamless capsule may be a seamless capsule of a three-layered structure, in which the shell film material layer 2 includes an inner shell film layer 4 such as a protective layer and a shell film layer 3.

Figure 3:
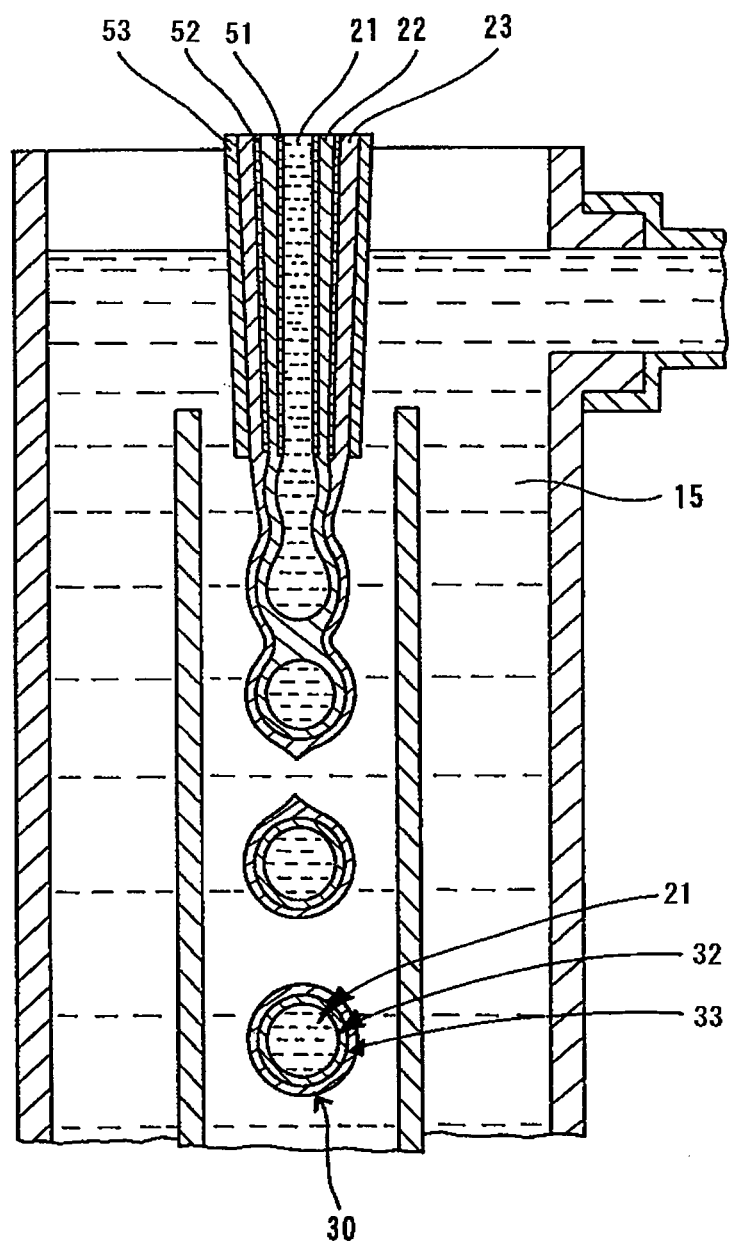
FIG. 3 is a schematic longitudinal section illustrating one embodiment of the nozzle portion of the apparatus for making one embodiment (three-layered structure) of the seamless capsule for exterminating insect pests of the present invention.

In a method of making the seamless capsule of a three-layered structure, as shown in FIG. 3, it is possible to continuously obtain a seamless capsule of a three-layered structure 30 by supplying a composition containing a content material to be enclosed 21 comprising an active ingredient for exterminating insect pests to the inner nozzle 51, supplying an inner shell film layer material 22 to the intermediate nozzle 52, supplying a shell film material composition 23 to the outer nozzle 53, respectively with a concentric triple nozzle; and simultaneously ejecting them through an each annular hole tip into a carrier fluid 15 flowing down. Examples of the carrier fluid include, for example, a medium-chain fatty acid triglyceride (MCT), a long-chain fatty acid triglyceride, vegetable fats and oils (palm oil, olive oil, sunflower oil, rapeseed oil, safflower oil, sesame oil, rapeseed oil, grape seed oil, and mixtures thereof etc.), silicone oils (dimethyl silicone, etc.), liquid paraffin and mixtures thereof. Long-chain fatty acid triglycerides, specifically, liquid oil having a fatty acid composition of oleic acid (60 to 70%), linoleic acid (10 to 15%), stearic acid (5 to 10%) and palmitic acid (10 to 15%) or olive oil are preferred. For more information on the manufacturing process and other materials used in the above process, it is possible to use the processes and materials described in JP 2007-145756 A.

Furthermore, in the seamless capsule of the three-layered structure shown in FIG. 2 comprising the content material, the protective layer of the content material and the shell film layer, it may be a seamless capsule of a four-layered structure which further comprises a layer containing an objective active ingredient between the protective layer of the content material to be enclosed and the shell film layer, or a seamless capsule of a four or more-layer structure, in which the layer containing an objective active ingredient or the protective layer is formed into an inner shell film layer of a multilayer structure. For a method of making the seamless capsule of the four or more-layered structure, it is possible to use the method described in JP 2007-145756 A.

Examples of a dispersion medium or a solvent for a lipophilic (hydrophobic) active ingredient for exterminating insect pests include a medium-chain fatty acid triglyceride (MCT), a long-chain fatty acid triglyceride, vegetable fats and oils (palm oil, olive oil, sunflower oil, safflower oil, sesame oil, rapeseed oil, grape seed oil, and mixtures thereof etc.), silicone oils (dimethyl silicone, etc.), liquid paraffin, SAIB (sucrose acetate isobutyrate) and mixtures thereof. Furthermore, examples of a dispersion medium or a solvent for a hydrophilic active ingredient for exterminating insect pests include polyethylene glycols, glycerin, propylene glycol, polypropylene glycol and mixtures thereof. Long-chain fatty acid triglycerides, specifically, liquid oil having a fatty acid composition of oleic acid (60 to 70%), linoleic acid (10 to 15%), stearic acid (5 to 10%) and palmitic acid (10 to 15%) or olive oil are preferred.

From the point of view of repellency and transportability of termites, controlled-release and an environmental influence of the active ingredient for exterminating insect pests, a seamless capsule for exterminating insect pests using a combination of:

gelatin as a substrate of the shell film material layer; and as a composition containing a content material to be enclosed, a suspension or a dispersion of olive oil as a dispersion medium and a powder of an active ingredient for exterminating insect pests insoluble in it is preferred.

As described above, when using gelatin as a substrate of the shell film material layer, a method of making the seam capsule for exterminating insect pests of the present invention comprises the steps of:

(a) forming a seamless capsule comprising a content material to be enclosed as an active ingredient for exterminating insect pests and at least one shell film material layer including the content material therein with a concentric multiple nozzle having at least an inner nozzle and an outer nozzle concentrically arranged, of which a radius is sequentially increased as shown in FIG. 3, (b) cross-linking gelatin of the shell film material layer with an aldehyde as a cross-linking agent, (c) inactivating the aldehyde with a neutralizing agent after the cross-linking reaction, (e) drying it, and (f) coating an egg recognition pheromone on the surface of the seamless capsule.

As the step (b), specifically, a method of cross-linking the gelatin of the shell film material layer by dipping the seamless capsule formed in the step (a) in a solution of the aldehyde as a cross-linking agent before drying the seamless capsule may be performed, but it is not limited thereto.

Similarly, as the above step (c), specifically, a method of inactivating the seamless capsule after the cross-linking reaction by taking out the seamless capsule from the aldehyde solution to dip it in a solution of the neutralizing agent may be performed, but it is not limited thereto.

Furthermore, it is possible to immobilize the egg recognition pheromone or a main component thereof on the shell film material layer by performing the step (f) of coating an egg recognition pheromone on the surface of the seamless capsule after the step (a) of forming a seamless capsule, and then performing the step (b) of cross-linking gelatin of the shell film material layer with an aldehyde as a cross-linking agent. It is desired that a coating amount of the egg recognition pheromone is within the range of 0.01 to 5% by mass, preferably 0.02 to 2% by mass, based on the total mass of the shell film material layer. When the coating amount of the egg recognition pheromone is smaller than 0.01% by mass, termites cannot recognize the seamless capsule as eggs thereof. On the other hand, when the coating amount is larger than 5% by mass, the egg recognition effect is not changed, but the consumption amount of the expensive main component of the egg recognition pheromone is increased, which is uneconomical.

The egg recognition pheromone or the main component thereof may be coated on the surface of the finished seamless capsule as described in the step (f), but may be previously incorporated into the shell film material layer in the step (a) of forming the seamless capsule. It is desired that an amount of the egg recognition pheromone in that case is within the range of 0.01 to 10% by mass, preferably 0.02 to 5% by mass, based on the total mass of the shell film material layer. When the amount of the egg recognition pheromone is smaller than 0.01% by mass, termites cannot recognize the seamless capsule as eggs thereof. On the other hand, when the coating amount is larger than 10% by mass, the egg recognition effect is not changed, but the consumption amount of the expensive main component of the egg recognition pheromone is increased, which is uneconomical. Furthermore, it is possible to immobilize the egg recognition pheromone or the main component thereof in the shell film material layer by forming the seamless capsule, in which the egg recognition pheromone or the main component thereof is previously incorporated into the shell film material layer, and then cross-linking the gelatin of the shell film material layer with the aldehyde as the cross-linking agent.

It is preferable that the main component of the egg recognition pheromone is β-glucosidase and/or lysozyme as described above. When using both of the β-glucosidase and lysozyme, as described above, there are the method of coating them on the surface and the method of forming the seamless capsule, in which they are previously incorporated into the shell film material layer, as a method of adding them to the shell film material layer. In addition, they may be immobilized or not, respectively. Therefore, for example, an embodiment that one of β-glucosidase and lysozyme as the main component of the egg recognition pheromone is immobilized in the shell film material layer and the other is coated on the seamless capsule without immobilizing it, is also within the scope of the present invention.

An aldehyde used as the cross-linking agent is preferably glutaraldehyde. A neutralizing agent of the aldehyde is preferably a hypochlorous acid, amino acids and/or alkali metal salts thereof. The amino acids and/or alkali metal salts thereof are preferably soluble in water at least at room temperature, and are more preferably at least one selected from the group consisting of glycine, alanine, arginine, proline and sodium glutamate.

It is desired that the amount of the cross-linking agent is within the range of 1 to 20% by mass, preferably 5 to 10% by mass, based on the total mass of the shell film material layer. When the amount of the cross-linking agent is smaller than 1% by mass, a cross-linking reaction becomes non-uniform. On the other hand, when the amount is larger than 20% by mass, it takes time to remove the residual cross-linking agent.

It is desired that the amount of the neutralizing agent is within the range of 3 to 15% by mass, preferably 4 to 10% by mass, based on the total mass of the shell film material layer. When the amount of the neutralizing agent is smaller than 3% by mass, the neutralization becomes non-uniform. On the other hand, when the amount is larger than 15% by mass, it takes time to remove the residual neutralizing agent.

Furthermore, as a pH adjusting agent, from 0.01 to 10% by mass of an organic acid, such as sodium acetate, may be coated on the surface of the seamless capsule, based on the total mass of the shell film material layer. In particular, acetic acid and sodium acetate as a salt thereof among the organic acids have also an antifungal effect.

In addition, in the method of making a seamless capsule, a powdery releasing agent (dusting powder), such as corn starch, silica gel and the like has been usually used for seamless capsules formed through a concentric multiple nozzle in order to easily handle it between the steps before the drying step. As described above, the inventors have found that the characteristics of the seamless capsule, particularly a surface roughness (Ra) is an important factor in the egg recognition of termites. However, the inventors have also found that the seamless capsules, in which the powdery releasing agent is used, have very large surface roughness because of the residual powdery releasing agent, although the seamless capsules are cleaned with a solvent and the like before drying. Therefore, in the present invention, it was possible to improve a transporting rate of the agent for exterminating insect pests (imitation eggs) by reducing the surface roughness (Ra) with a liquid releasing agent such as silicone oil, olive oil and the like without using the conventional powdery releasing agent.

Furthermore, if using poisons which termites do not exhibit repellency such as fipronil, chlorfenapyr, imidacloprid, chlorpyrifos and the like described in JP 2004-500043 A as the active ingredient for exterminating insect pests used in the present invention, the active ingredient is not necessarily arranged inside of the shell film material layer as a content material to be enclosed and may be included only in the shell film material layer. Consequently, the seamless capsule for exterminating insect pests of the present invention also includes a capsule having no content material to be enclosed. Therefore, the term "seamless capsule for exterminating insect pests", particularly "capsule" as used herein includes capsules that contain the active ingredient for exterminating insect pests and egg recognition pheromone and do not contain the content material to be enclosed, that is, capsules consisting of only a substrate of the shell film material layer such as gelatin. Further, in the case of capsules of a three-layered structure, in which a protective layer is arranged between the content material to be enclosed and the shell film material layer, the active ingredient for exterminating insect pests may be included in not only the shell film material layer, but also the protective layer.

In another embodiment, the present invention provides a method of exterminating insect pests, wherein a seamless capsule imitating an egg of an insect pest for exterminating insect pests comprising a content material to be enclosed and a shell film material layer including the content material therein, wherein an active ingredient for exterminating insect pests is contained in the content material and/or the shell film material layer, an egg recognition pheromone is coated on the surface of the seamless capsule, and the seamless capsule has a surface roughness (Ra) of 0.005 to 5 µm is supplied to the insect pests, and is transported in a nest by utilizing an egg transporting behavior of the insect pests. Insect pests exterminated by the method of the present invention may be any insect pests as long as they have an egg transportation instinct by the egg recognition pheromone. An insect pest, to which the method of exterminating insect pests of the present invention is preferably applied, is a termite. For example, when exterminating termites, a seamless capsule for exterminating insect pests imitating an egg of the insect pest which the egg recognition pheromone of the present invention is coated on the surface thereof, can be put on an ant road or a part of a nest material. After forming a hole in the ant road by a drill, the agent for exterminating insect pests can be put therein. In addition, the agent for exterminating insect pests can be wrapped with a protective film of, for example, cellophane for retaining durability thereof in the outdoors. In such case, a substance that promotes food ingestion, such as wood extract, decayed wood extract can be added to the protective film. It is also effective to use a monitoring station in the method of exterminating insect pests of the present invention.

EXAMPLES (Preparation of Egg Recognition Pheromone)

Egg recognition activities of a termite egg extract, β-glucosidase, egg-white lysozyme, cellulase, a mixture of egg-white lysozyme and cellulase, a mixture of egg-white lysozyme and β-glucosidase, a mixture of egg-white lysozyme, β-glucosidase and cellulase, and an 50% glycerin aqueous solution as a control were investigated by using a *Reticulitermes speratus* worker (worker termites).

Each test sample was prepared as follows.

Ultrapure water of 800 µL was added to 400 mg of *Reticulitermes speratus* eggs in an Eppendorf tube, homogenized, and subjected to ultrasonic treatment for 5 minutes, and centrifugation was performed at 15,000 rpm for 30 minutes. The supernatant was lyophilized, and 5.0 mg of the lyophilized powder was dissolved in 100 µL of a 30% glycerin aqueous solution (termite egg extract). A β-glucosidase derived from an almond (Product#: G0395-5KU, Lot#: 047K4037, SIGMA-ALDRICH) of 1.0 mg was dissolved in 10 µL of a 50% glycerin aqueous solution (β-glucosidase). A chicken egg-white lysozyme (Product#: L7651-10G, Lot#: 056K16901, SIGMA-ALDRICH) was desalted using a dialysis membrane SnakeSkin (7000MWCO, Product#: 68700, PIERCE) and then 2.0 mg of the desalted chicken egg-white lysozyme was dissolved in 10 µL of a 50% glycerin aqueous solution (egg-white lysozyme). A cellulase derived from trichoderma viridae (Product#: C1794-5KU, Lot#: 074K1304, SIGMA-ALDRICH) of 1.0 mg was dissolved in 10 μL of a 50% glycerin aqueous solution (cellulase).

An egg-white lysozyme of 2.0 mg and 1.0 mg of cellulose were dissolved in 10 μL of a 50% glycerin aqueous solution (a mixture of egg-white lysozyme and cellulase). An egg-white lysozyme of 2.0 mg and 1.0 mg of β-glucosidase were dissolved in 10 μL of a 50% glycerin aqueous solution (a mixture of egg-white lysozyme and β-glucosidase). An egg-white lysozyme of 2.0 mg, 1.0 mg of β-glucosidase and 1.0 mg of cellulose were dissolved in 10 μL of a 50% glycerin aqueous solution (a mixture of egg-white lysozyme, β-glucosidase and cellulase).

The egg-white lysozyme 2.0 mg and 1.0 mg cellulase were dissolved in 50% glycerin aqueous solution of 10 μL (a mixture of egg-white lysozyme and cellulase). The egg-white lysozyme 2.0 mg and β-glucosidase 1.0 mg was dissolved in 50% glycerin aqueous solution of 10 μL (a mixture of egg-white lysozyme and β-glucosidase). Egg-white lysozyme 2.0 mg and β-glucosidase 1.0 mg, and 1.0 mg cellulase it was dissolved in 50% glycerin aqueous solution of 10 μL (a mixture of egg-white lysozyme and β-glucosidase and cellulase) to obtain the egg recognition pheromone of the present invention.

(Production of Seamless Capsule)

Method 1: In Case of Thermoplastic Shell

A capsule manufacturing apparatus having a concentric triple nozzle shown in FIG. 3 was set up, and olive oil cooled to 8° C. as a carrier fluid 15 was circulated therein. A shell film material composition 23 was ejected through the outer nozzle 53 of the apparatus, a hydrophobic material 22 was ejected through the intermediate nozzle 52, and an content material-containing composition 21 was ejected through the inner nozzle 51, respectively, into the carrier fluid 15 such that the ejection rate of the three-phase composite jet formed is constant (540 mm/second) to obtain a seamless capsule 30 of the three-layered structure (FIG. 2). In the case that the content material-containing composition is a hydrophobic material, a seamless capsule of a two-layered structure (FIG. 1) only consisting of a shell film material composition and a content material-containing composition may be prepared by using a concentric double nozzle.

After the resulting capsules were dried with a ventilation type rotary drier at a temperature of 25° C. and a humidity of 50% RH, they were used in the evaluation test as described later.

Method 2: In Case of Ultraviolet Curable Shell

A capsule manufacturing apparatus manufactured by Morishita Jintan Co., Ltd. having a concentric triple nozzle shown in FIG. 3 was set up, and dimethyl silicone cooled to 15° C. as a carrier fluid 15 was circulated therein. A shell film material composition 23 containing benzophenone as a photo-initiator was ejected through the outer nozzle 53 of the apparatus, a hydrophobic material 22 was ejected through the intermediate nozzle 52, and a content material-containing composition 21 was ejected through the inner nozzle 51, respectively, into the carrier fluid 15 such that the ejection rate of the three-phase composite jet formed is constant (540 mm/second) to obtain a seamless capsule 30 of the three-layered structure (FIG. 2).

The capsules in the carrier fluid were irradiated with ultraviolet rays using a metal halide lamp (wavelength of 320 to 400 nm), and the photo-curable resin was polymerized. In this way, seamless capsules having a diameter of 1 mm were obtained at a rate of 24,000 capsules per minute. After the resulting capsules were dried with a ventilation type rotary drier at a temperature of 25° C. and a humidity of 50% RH, it was found that they had a final diameter of 0.5 mm. The resulting capsules after drying were used in the evaluation test as described later. The test methods are as described later.

Example 1

A seamless capsule having a two-layered structure (a diameter of 0.5 mm, a shell film content of 40%, a hydramethylnon content of 1 μg/particle, a liquid release agent: silicone oil) was prepared by using gelatin as a shell film material composition and using hydramethylnon as a content material-containing composition in Method 1. As a sample for the evaluation test (I), an agent for exterminating insect pests was obtained by adding 1.0 μL of the egg recognition pheromone described above to 3.5 mg of the capsules (50 capsules) and well mixing them to coat the egg recognition pheromone on the capsules. As a sample for the evaluation test (II), an agent for exterminating insect pests was obtained by adding 80 μL of the egg recognition pheromone described above to 280 mg of the seamless capsules (4000 capsules) and well mixing them to coat the egg recognition pheromone on the capsules. A transporting rate of the resulting agent for exterminating insect pests (imitation eggs) and a mortality rate of the termites were evaluated. The results thereof are shown in the following Table 1.

Example 2

A transporting rate of the agent for exterminating insect pests coated with the egg recognition pheromone and a mortality rate of the termites were evaluated as described in Example 1, except that a seamless capsule was prepared by using a photocross-linked chitosan (which is formed by introducing lactic acid and azide groups into chitosan and causes gelation by an ultraviolet irradiation) as the shell film material composition in Method 2 (a liquid release agent: silicone oil). The results thereof are also shown in the following Table 1.

Example 3

A transporting rate of the agent for exterminating insect pests coated with the egg recognition pheromone and a mortality rate of the termites were evaluated as described in Example 1, except that a seamless capsule of a three-layered structure was prepared by using a hydroxyethyl methacrylate oligomer as the shell film material composition, using a mixture liquid of trichlorfon in polyethylene glycol 400 as the content material-containing composition and using SAIB (sucrose acetate isobutyrate) as the hydrophobic substance for a protective layer in Method 2. The results thereof are also shown in the following Table 1.

Comparative Example 1

A seamless capsule having a two-layered structure (a diameter of 0.5 mm, a shell film content of 40%, a hydramethylnon content of 1 μg/particle, a powder release agent: corn starch) was prepared by using gelatin as a shell film material composition and using hydramethylnon as a content material-containing composition in Method 1. As a sample for the evaluation test (I), an agent for exterminating insect pests was obtained by uniformly mixing 50 number equivalents of the seamless capsules and 50 number equivalents of glass beads having a diameter of 0.5 mm, and then adding 2.0 μL of the egg recognition pheromone described above thereto and well mixing them to coat the egg recognition pheromone thereon. As a sample for the evaluation test (II), an agent for exterminating insect pests was obtained by uniformly mixing 4000 number equivalents of the seamless capsules and 4000 number equivalents of glass beads having a diameter of 0.5 mm, and then adding 160 μL of the egg recognition pheromone described above thereto and well mixing them to coat the egg recognition pheromone thereon. A transporting rate of the resulting each agent for exterminating insect pests (imitation eggs) and a mortality rate of the termites were evaluated. The results thereof are shown in the following Table 1.

Comparative Example 2

A transporting rate of the agent for exterminating insect pests and a mortality rate of the termites were evaluated as described in Comparative Example 1, except that chitosan was used as the shell film material composition. The results thereof are also shown in the following Table 1.

Comparative Example 3

A transporting rate of the agent for exterminating insect pests and a mortality rate of the termites were evaluated as described in Comparative Example 1, except that a seamless capsule of a three-layered structure was prepared by using a hydroxyethyl methacrylate oligomer as the shell film material composition, using a mixture liquid of trichlorfon in polyethylene glycol 400 as the content material-containing composition and using SAIB (sucrose acetate isobutyrate) as the hydrophobic substance for a protective layer in Method 2. The results thereof are also shown in the following Table 1.

Comparative Example 4

A transporting rate of the agent for exterminating insect pests and a mortality rate of the termites were evaluated by using the seamless capsule prepared in Comparative Example 1 is used alone (without glass beads). The results thereof are also shown in the following Table 1.

(Test Method)

(1) Surface Roughness (Ra)

The surface roughness (Ra) is calculated from data measured by an image analysis of a seamless capsule for exterminating insect pests comprising a content material which is an active ingredient for exterminating insect pests as a measurement sample with a shape measurement laser microscope ("VK-X100" or "VK-X200" manufactured by Keyence Corporation).

(2) Young's Modulus

The Young's modulus was calculated from a measurement value of a slope of the "stress-strain curve" obtained by a compression test, which is a mechanical test method, with a particle hardness tester "GRANO" manufactured by Okada Seiko CO., LTD. with respect to a seamless capsule for exterminating insect pests comprising a content material which is an active ingredient for exterminating insect pests as a measurement sample.

(3) Density

The density was calculated from the volume and mass of a seamless capsule for exterminating insect pests comprising a content material which is an active ingredient for exterminating insect pests as a solid sample, which was directly measured by a density measurement method due to a geometric measurement according to JIS 8807.

(4) Evaluation Test (I)

The 50 resulting agents for exterminating insect pests in Example and 100 resulting agents for exterminating insect pests in Comparative Example (including 50 glass beads) were randomly put on a petri dish having a diameter of 35 mm and a depth of 15 mm, and then 10 *Reticulitermes speratus* workers (worker termites) were put therein, respectively. After the petri dishes were placed still at 25° C. for 24 hours in a thermostatic chamber, a transporting rate of the agent for exterminating insect pests (imitation eggs) into egg mass was evaluated. In addition, a mortality rate of the termites in the petri dish was evaluated. The results thereof are shown in the following Table 1.

(5) Evaluation Test (II)

Figure 4:
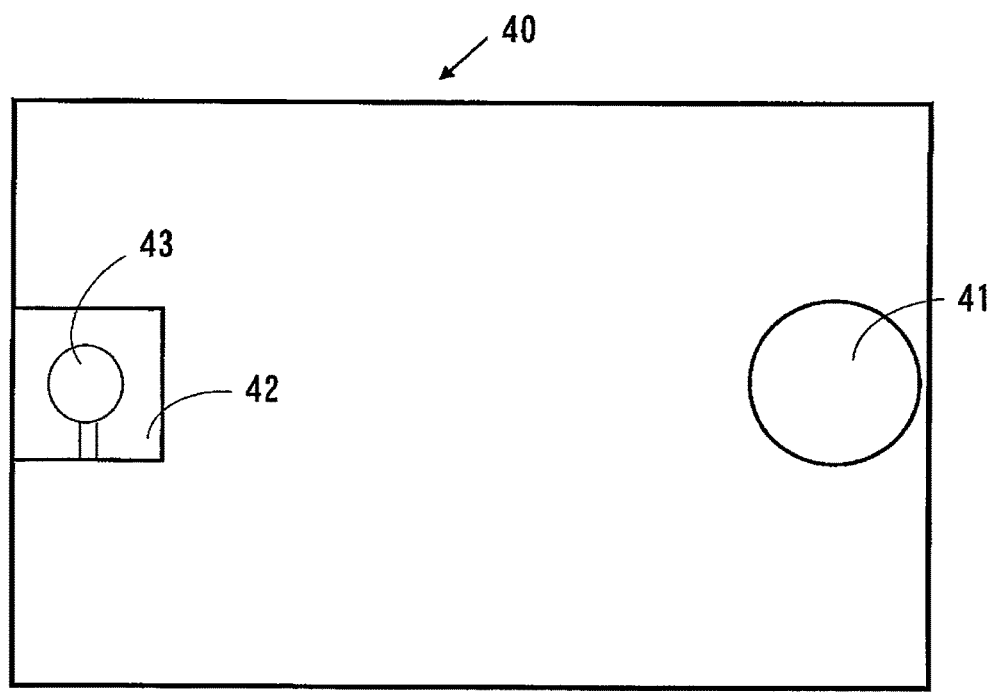
FIG. 4 is a schematic top view illustrating the large case having an artificial nest and an installation location of an agent for exterminating insect pests in an installation station of an agent for exterminating insect pests, used in the evaluation test (II) of Examples of the present invention.

As shown in FIG. 4, an artificial nest of termites obtained by blending a cellulose in a brown decayed wood was set in a large scale rectangular styrene case, and 4000 resulting agents for exterminating insect pests in Example and 8000 resulting agents for exterminating insect pests in Comparative Example (including 4000 glass beads) were put on an installation location of the agent for exterminating insect pests in the center of the upper surface of an installation station of the agent, and then 400 *Reticulitermes speratus* workers (worker termites) were put therein, respectively. After the styrene cases were placed still at 25° C. for 24 hours in a thermostatic chamber, a transporting rate of the agent for exterminating insect pests (imitation eggs) into egg mass in the artificial nest was evaluated. In addition, a mortality rate of the termites in the artificial nest was evaluated. The results thereof are shown in the following Table 1.

The size of the case and the like is as follows:

Large size case: 221×141×37 mm

Artificial nest of termites: 40 mm diameter×30 mm height

Installation station of the agent for exterminating insect pests: 40×40×30 mm

Installation location of the agent for exterminating insect pests: 15 mm diameter×10 mm depth (Test Results)

TABLE 1

|  | Example | | |
|---|---|---|---|
|  | 1 | 2 | 3 |
| Surface roughness Ra [μm] | 0.02 | 0.07 | 0.04 |
| Young's modulus [MPa] | 2.94 | $1 \times 10^3$ | 2.83 |
| Density [g/cm$^3$] | 1.02 | 1.08 | 1.05 |
| Diameter [μm] | 500 | 500 | 500 |
| Evaluation test (I) | | | |
| Transporting rate (%) | 100 | 100 | 100 |
| Mortality rate (%) | 100 | 100 | 100 |
| Evaluation test (II) | | | |
| Transporting rate (%) | 96 | 89 | 87 |
| Mortality rate (%) | 100 | 83 | 79 |

|  | Comparative Example | | | |
|---|---|---|---|---|
|  | 1 | 2 | 3 | 4 |
| Surface roughness Ra [μm] | 6.0 | 7.5 | 5.5 | 6.0 |
|  | 0.03$^G$ | 0.03$^G$ | 0.03$^G$ |  |
| Young's modulus [MPa] | $7 \times 10^{4G}$ | $7 \times 10^{4G}$ | $7 \times 10^{4G}$ | 2.94 |
| Density [g/cm$^3$] | 2.5$^G$ | 2.5$^G$ | 2.5$^G$ | 1.02 |
| Diameter [μm] | 500$^G$ | 500$^G$ | 500$^G$ | 500 |

TABLE 1-continued

| Evaluation test (I) | | | | |
|---|---|---|---|---|
| Transporting rate (%) | 100 | 100 | 100 | 0 |
| Mortality rate (%) | 100 | 100 | 100 | 0 |
| Evaluation test (II) | | | | |
| Transporting rate (%) | 87 | 77 | 75 | 0 |
| Mortality rate (%) | 53 | 48 | 45 | 0 |

G: Glass beads

Since a transport distance in the test using the large case of the evaluation tests (II) is longer as compared with the test using a petri dish of evaluation tests (I), it was seen in the agents for exterminating insect pests of Comparative Examples that the capsules were separated from the glass beads on the way of the transport by termites and the termites left the agents on the way to the nest, and the transporting rate of the capsules, in which an active ingredient for exterminating insect pests is contained, of Comparative Examples was lower than that of Examples (A ratio of the glass beads was high in the agent for exterminating insect pests of Comparative Examples transported to the nest).

Therefore, it was seen that the mortality rates of Comparative Examples were lower than those of Examples, because the capsules, in which an active ingredient for exterminating insect pests is contained, were separated from the glass beads during transporting and many capsules were not transported to the nest.

On the other hand, it was seen that the capsules, in which an active ingredient for exterminating insect pests is contained, were efficiently transported to the nest, because the transporting rate by termites of the seamless capsules for exterminating insect pests of the present invention was high. Thereby, it was able to accomplish excellent mortality rate as compared with Comparative Examples.

INDUSTRIAL APPLICABILITY

Since the present invention provides an effective extermination of insect pests, particularly termites, it is applicable in an insecticide production industry, an insect pest extermination industry, a building industry, a landscape construction industry and the like. The present invention can also be utilized in the field of biological research.

DESCRIPTION OF REFERENCE NUMERALS

1: Content material
2: Shell film material layer
3: Shell film layer
4: Shell film inner layer
10: Seamless capsule for exterminating insect pests (two-layered structure)
20, 30: Three-layered structure capsule
15: Carrier fluid
21: Content material-containing composition
22: Solution for shell film inner layer
23: Shell film material solution
40: Large case for evaluation test
41: Artificial nest
42: Installation station of agent for exterminating insect pests
43: Installation location of agent for exterminating insect pests
51: Inner nozzle
52: Middle nozzle
53: Outer nozzle

What is claimed is:

1. A seamless capsule for exterminating insect pests, the seamless capsule comprising:
a content material to be enclose; and
a shell film material layer including the content material therein,
wherein the seamless capsule imitates an egg of the insect pests,
an active ingredient for exterminating the insect pests is contained in the content material, or the shell film material layer, or a combination thereof,
an egg recognition pheromone is coated on a surface of the seamless capsule, and
the seamless capsule has a surface roughness (Ra) in a range from 0.005 to 5 μm.

2. The seamless capsule for exterminating insect pests according to claim 1 having a Young's modulus in a range from 0.392 MPa to $20.6 \times 10^4$ MPa.

3. The seamless capsule for exterminating insect pests according to claim 1, having a density in a range from 0.5 to 9.0 g/cm$^3$.

4. The seamless capsule according to claim 1, having a diameter in a range from 250 to 600 μm.

5. The seamless capsule for exterminating insect pests according to claim 1, further comprising a protective layer formed from a shell film inner layer material between the content material and the shell film material layer.

6. The seamless capsule for exterminating insect pests according to claim 1,
wherein the insect pests are termites.

7. A method of exterminating insect pests, the method comprising:
supplying the seamless capsule for exterminating insect pests according to claim 1 to the insect pests,
wherein the seamless capsule is transported in a nest by utilizing an egg transporting behavior of the insect pests.

8. The seamless capsule for exterminating pests according to claim 6, wherein the seamless capsule has a diameter of about 200 μm to about 600 μm when the seamless capsule is spherical in shape, and a short diameter of about 200 m to about 600 μm when the seamless capsule has an elongated egg-shape.

* * * * *